US012667495B2

(12) United States Patent
    Cotton

(10) Patent No.: US 12,667,495 B2
(45) Date of Patent: Jun. 30, 2026

(54) WOUND DRESSING

(71) Applicant: BRIGHTWAKE LIMITED,
    Nottinghamshire (GB)

(72) Inventor: Stephen Cotton, Nottinghamshire (GB)

(73) Assignee: BRIGHTWAKE LIMITED,
    Nottinghamshire (GB)

( * ) Notice: Subject to any disclaimer, the term of this
    patent is extended or adjusted under 35
    U.S.C. 154(b) by 371 days.

(21) Appl. No.: 18/024,434

(22) PCT Filed: Sep. 3, 2021

(86) PCT No.: PCT/GB2021/000098
    § 371 (c)(1),
    (2) Date: Mar. 2, 2023

(87) PCT Pub. No.: WO2022/049363
    PCT Pub. Date: Mar. 10, 2022

(65) Prior Publication Data
    US 2023/0240900 A1     Aug. 3, 2023

(30) Foreign Application Priority Data

Sep. 3, 2020   (GB) ...................................... 2013871
    Aug. 5, 2021   (GB) ...................................... 2111315

(51) Int. Cl.
    *A61F 13/00*       (2024.01)
    *A61F 13/02*       (2006.01)
    *A61F 13/0246*     (2024.01)
(52) U.S. Cl.
    CPC ........ *A61F 13/023* (2013.01); *A61F 13/0253*
    (2013.01); *A61F 2013/00697* (2013.01)

(58) Field of Classification Search
    None
    See application file for complete search history.

(56) References Cited

U.S. PATENT DOCUMENTS 2,992,644  A      7/1961   Plantinga
    3,121,021  A      2/1964   Copeland
    2010/0159192 A1*  6/2010   Cotton ..................... A61L 15/58
                                                              428/137
                        (Continued)

FOREIGN PATENT DOCUMENTS

CN         207898589         9/2018
    EP              2382069 B1 *  8/2017   ............. A61F 13/02
                        (Continued)

OTHER PUBLICATIONS

JP 2001524357 A translation (Year: 2001).*
                        (Continued)

*Primary Examiner* — Kim M Lewis
(74) *Attorney, Agent, or Firm* — Troutman Pepper Locke,
LLP

(57) ABSTRACT

Wound dressings displaying improved adhesion and breathability and methods for their manufacture, the wound dressing comprising a backing layer, a layer of pressure-sensitive adhesive and a perforated layer of silicone gel, wherein the layer of pressure-sensitive adhesive is disposed between the substrate and the perforated layer of silicone gel, and wherein the layer of pressure-sensitive adhesive is moisture-permeable.

23 Claims, 6 Drawing Sheets

(56)    References Cited

U.S. PATENT DOCUMENTS

| | | | |
|---|---|---|---|
| 2014/0024989 A1* | 1/2014 | Ueda .................. | A61F 13/0253 |
| | | | 602/44 |
| 2016/0120706 A1 | 5/2016 | Collinson et al. | |
| 2017/0079846 A1 | 3/2017 | Locke et al. | |

FOREIGN PATENT DOCUMENTS

| | | | |
|---|---|---|---|
| JP | 2001524357 A | * | 12/2001 |
| WO | 99/27975 A1 | | 6/1999 |
| WO | 00/32142 A1 | | 6/2000 |
| WO | 2007/113597 A2 | | 10/2007 |
| WO | 2010/061228 A1 | | 6/2010 |
| WO | 2014/097069 A1 | | 6/2014 |
| WO | 2015/179235 A1 | | 11/2015 |

OTHER PUBLICATIONS

International Search Report and Written Opinion for International Application No. PCT/GB2021/000098 (mailed Dec. 22, 2021).
Great Britain Search Report under Section 17 for GB2013871.5 (dated Feb. 10, 2021).

* cited by examiner

WOUND DRESSING

This application is a national stage application under 35 U.S.C. § 371 of International Application No. PCT/GB2021/000098, filed Sep. 3, 2021, which claims the priority benefit of GB Patent Application No. 2013871.5, filed Sep. 3, 2020, and GB Patent Application No. 2111315.4, filed Aug. 5, 2021, all of which are hereby incorporated by reference in their entirety.

FIELD

This invention relates to a wound dressing. More particularly, this invention relates to a wound dressing displaying improved adhesion and breathability.

BACKGROUND

Different types of wound dressing are required to meet different clinical needs and there is an ongoing need to provide improved wound dressings. No single wound dressing product is suitable for use in all wound types or at all stages of healing.

However, a common requirement of a wound dressing is that it comprises an adhesive layer to retain it in place on the skin. At the same time, it is important that it is possible to remove the dressing from the skin without causing either damage to the underlying tissue, or pain and trauma to the patient.

Some types of wound also benefit particularly from a breathable wound dressing. For example, wounds that produce a relatively large quantity of wound exudate particularly benefit from a breathable dressing to reduce the rate at which moisture builds up in the wound environment and hence increase the wear-time for the dressing and keep the skin surrounding the wound healthy.

It is well known for wound dressings to have a silicone gel wound-contact layer, such as those described in patent application EP2561843. Hydrophobic silicone gels (commonly known as soft silicones) adhere readily to dry skin but do not stick to the surface of a moist wound and do not cause damage on removal. This makes them particularly suited for use as the wound contact layer in a wound dressing. However, it has been found that on some wounds, particularly heavily exuding wounds, the adhesion provided by a soft silicone wound contact layer may be insufficient and the dressing may become displaced during use.

WO2014/097069 attempts to overcome this issue through the addition of a pressure-sensitive adhesive, which adheres more strongly to the skin than silicone gel. The disclosed island wound dressing comprises (in sequence) a backing sheet, a continuous layer of pressure-sensitive adhesive, an island of absorbent material, and an apertured layer of silicone gel, with the apertured layer of silicone gel forming the wound contacting surface. In the region of the wound dressing surrounding the island of absorbent material the pressure-sensitive adhesive may contact the skin through the apertures in the layer of silicone gel, thus increasing the strength of the adhesion to the skin.

While the wound dressing disclosed in WO2014/097069 may provide stronger adhesion than a wound dressing in which the wound contacting layer is formed only of a layer of silicone gel, pressure-sensitive adhesives are typically impermeable to oxygen or moisture vapour, and the continuous layer of such an adhesive would create a non-breathable wound dressing. This results in an undesirable wound healing environment, particularly for exuding wounds. There is therefore a need for a new wound dressing, which has both strong adhesion and improved breathability.

SUMMARY

There has been developed a new wound dressing which overcomes or substantially mitigates the problems associated with the prior art.

DETAILED DESCRIPTION

According to a first aspect of the invention there is provided a wound dressing comprising a backing layer, a layer of pressure-sensitive adhesive and a perforated layer of silicone gel, wherein the layer of pressure-sensitive adhesive is disposed between the backing layer and the perforated layer of silicone gel, and wherein the layer of pressure-sensitive adhesive is moisture-permeable.

The perforated layer of silicone gel forms the wound contacting layer and the pressure-sensitive adhesive is exposed to the skin through the perforations in the silicone gel layer. The combination of silicone gel and pressure-sensitive adhesive improves adhesion of the dressing but prevents the wound dressing from adhering to the skin too firmly. At the same time, the moisture-permeable nature of the layer of pressure-sensitive adhesive reduces the rate at which moisture builds up between the dressing and the skin, thus increasing the wear-time for the dressing, including lengthening the time it takes for any absorbent component present to become saturated. This makes the dressing more convenient for the user and reduces the environmental impact of the dressing.

The pressure-sensitive adhesive may be any one of numerous pressure-sensitive adhesives known in the art. Such adhesives, generally in dry (solvent free) form, are aggressively and permanently tacky at room temperature and firmly adhere to a variety of dissimilar surfaces upon mere contact without the need for more than finger or hand pressure. They require no activation by water, solvent or heat in order to exert a strong adhesive holding force. Examples of pressure sensitive adhesives include rubber/resin adhesive, which is a mixture of a rubbery material and a hard resin, and acrylic (or acrylate) adhesives. The currently preferred class of pressure-sensitive adhesive for use in the present invention is acrylic adhesive.

The layer of pressure-sensitive adhesive is moisture-permeable and may have a moisture vapour transmission rate (MVTR) of at least 500 $g/m^2/24$ hr, or at least 1000 $g/m^2/24$ hr, or at least 1500 $g/m^2/24$ hr.

The layer of pressure-sensitive adhesive maybe coated onto the wound-facing surface of the backing layer and may extend across substantially the whole wound-facing surface of the backing layer.

The layer of pressure-sensitive adhesive may be a discontinuous layer of pressure-sensitive adhesive such that moisture can permeate through apertures in the layer of adhesive. The discontinuous layer of pressure-sensitive adhesive may extend across the whole surface of the backing layer. The layer of pressure-sensitive adhesive may be irregularly discontinuous, such that apertures in the layer of adhesive occur in a random manner, and do not form a regular array. The apertures may be closely-spaced. The apertures in the layer of adhesive may be irregularly shaped and/or sized. The apertures in the layer of pressure-sensitive adhesive may alternatively form a regular array, and may be circular, square, oval, polygonal or any other appropriate shape.

The layer of pressure-sensitive adhesive may be fibrous, such that it is formed from intermingling fibres of adhesive that may form a regular or irregular mat or mesh on the backing layer. An irregular mat may be formed by the intermingling of monofilament fibres of adhesive, creating an open, net-like structure on the surface of the backing layer. Such a layer of pressure-sensitive adhesive may comprise a plurality of closely-spaced apertures or gaps in the adhesive. The apertures or gaps in a fibrous layer of pressure-sensitive adhesive may not be a series of discrete apertures, but may instead be an intermingling array of irregularly formed gaps in the pressure-sensitive adhesive. Moisture may permeate through these apertures in the layer of pressure-sensitive adhesive.

The layer of pressure-sensitive adhesive may be porous, such that moisture can permeate through the pores in the layer of adhesive. The pores may form a regular array, or may form a random pattern. Where the pores form a random pattern, they may vary in size.

The apertures or gaps in the layer of pressure-sensitive adhesive may vary in size but are typically smaller than the perforations in the layer of silicone gel. The apertures in the layer of pressure-sensitive adhesive may have a mean average area of from 0.1 $mm^2$ to 5 $mm^2$, or from 0.1 $mm^2$ to 4 $mm^2$, or from 0.1 $mm^2$ to 3 $mm^2$.

The apertures in the layer of pressure-sensitive adhesive may account for at least for at least 1%, at least 3%, at least 5%, at least 10%, at least 20%, or at least 30%, of the area covered by the pressure-sensitive adhesive. The apertures in the layer of pressure-sensitive adhesive may account for up to 80%, or up to 70%, or up to 60%, or up to 50%, or up to 40% of the area covered by the pressure-sensitive adhesive. For example, the apertures in the layer of pressure-sensitive adhesive may account for between 1% and 80%, or between 10% and 70% of the area covered by the pressure-sensitive adhesive.

Where the apertures form a regular array, the apertures in the layer of pressure-sensitive adhesive must be in registration with the perforations in the overlying layer of silicone gel in order to permit moisture vapour to pass through the two layers. Where the apertures in the layer of pressure-sensitive adhesive form an irregular array, and in particular where they form an irregular array of closely-spaced apertures which are smaller than the perforations in the layer of silicone gel, sufficient apertures in the irregular array will come into registration with the perforations in the layer of silicone gel to permit moisture vapour to pass through, without it being necessary to purposefully line up the apertures in the two layers.

The backing layer most preferably has the form of a relatively thin film of a synthetic plastics material. A wide variety of plastics may be suitable for use as the backing layer. Examples include polyurethane, polyvinylchloride, polypropylene and regenerated cellulose. However, the currently preferred material for the backing layer is polyurethane.

The backing layer may have an MVTR of at least 300 $g/m^2/24$ h, or at least 500 $g/m^2/24$ hr, or at least 700 $g/m^2/24$ hr at 37° C. and 100% to 10% relative humidity difference.

The layer of pressure-sensitive adhesive as described above may extend across the whole surface of the backing layer. A layer of perforated silicone gel overlays the layer of pressure-sensitive adhesive and may extend across the whole wound contacting surface of the wound dressing, forming the wound contacting layer. Silicone gels are known for use as a wound contacting layer on a wound dressing as they cause the wound dressing to be retained in position when applied, yet are non-adherent such that they can be removed from the skin without causing significant disruption or trauma to the wound or the surrounding skin.

Suitable silicone gels are formed by reaction between two liquid components that are mixed together to produce a liquid silicone gel precursor composition immediately prior to application to a substrate. The precursor composition may then be spread onto the substrate before being cured to form a silicone gel, typically with the application of heat. Suitable components that are intended for such reaction to form a silicone gel are readily available commercially and are typically a vinyl substituted silicone and a hydride-containing silicone.

Accordingly, the silicone gel layer may be carried on a substrate layer. The low adherence of silicone gels can lead to a tendency for silicone gel layers to detach from a substrate and hence the substrate may have been treated in order to improve adherence of the silicone gel, such as by corona treatment or the application of a silicone primer. Alternatively, the substrate may have a porous surface that the liquid silicone gel precursor composition is able to soak into before it is cured into a gel, which produces a gel layer that is firmly keyed into the substrate.

The substrate may be a film of a synthetic plastics material, such as polyurethane, polyvinylchloride, polypropylene or regenerated cellulose. Suitable porous materials for the substrate are melt-blown materials, including melt-blown polyurethane.

The substrate may also carry an adhesive on the surface opposite to the layer of silicone gel to facilitate adherence of additional dressing components such as the backing film or absorbent pads.

In particular, the silicone gel may be carried on a silicone gel laminate as disclosed in WO 2007/113597.

The thickness and coating weight of the layer of silicone gel may vary depending on the properties of the gel and its intended application. In particular, the coating weight of the silicone gel may be between 50 $g/m^2$ and 800 $g/m^2$. However, the layer of silicone gel is preferably relatively thin in order to reduce the spacing between the moisture-permeable pressure-sensitive adhesive coating on the backing layer and the skin. Accordingly, the coating weight of the silicone gel is preferably less than 600 $g/m^2$, more preferably less than 400 $g/m^2$, more preferably less than 300 $g/m^2$, and most preferably about 200 $g/m^2$.

The perforations in the layer of silicone gel are preferably arranged regularly in order to ensure even adhesion of the dressing to the skin. The perforations will typically all be substantially the same shape and size although different shapes and/or sizes of perforation may be present in the same dressing. The perforations in the layer of silicone gel may be circular or substantially circular. The separation between adjacent perforations typically being comparable with, or greater than, the diameter or width of the perforations.

The size of perforation that is required to enable the moisture-permeable pressure-sensitive adhesive to contact the skill will vary depending on the thickness of the silicone gel layer or the spacing between the skin and the pressure-sensitive adhesive in the dressing, as well as other factors such as the elasticity of the backing layer. However, the perforations may typically have a diameter or width of between 1 mm and 15 mm, between 3 mm and 10 mm, between 5 mm and 8 mm in diameter, or about 6 mm.

The silicone gel may cover from 10-95% of the wound-facing surface, more commonly 30-95% of the wound contacting surface, more commonly 50-90% of the wound contacting surface of the dressing.

A range of methods for producing a perforated layer of silicone gel are known, including punching out or the use of high frequency mechanical vibrations as described in WO2010/061228. Accordingly, these or any other suitable method known in the art may be used in the manufacture and application of the perforated layer of silicone gel for use in the described invention.

The silicone gel layer overlays the layer of pressure-sensitive adhesive. The perforations in the silicone gel layer enable areas of the layer of pressure-sensitive adhesive to contact the skin through the perforations and thus increase the overall adhesion of the dressing to the skin. However, because a large proportion of the wound contacting surface is still formed from silicone gel, the wound dressing overall can still be removed from the skin without damage to the wound or surrounding skin. The perforations in the silicone gel layer also expose some of the moisture-permeable layer of pressure-sensitive adhesive, permitting the passage of water vapour through the wound dressing.

The wound dressing of the invention may comprise other features common to wound dressings. Thus, the wound dressing of the invention may be supplied with a releasable liner which covers the adhesive portions of the wound dressing prior to use, and which is removed from the dressing immediately before application of the dressing to the wound. Such releasable liners are commonly used on wound dressings known in the art, and suitable materials which can be employed in the present invention will be familiar to the skilled worker. For example, the releasable liner may be of a suitable plastics sheet or a siliconised paper or the like.

The wound dressing may also incorporate substances known to assist in wound healing, such as manuka honey, silver and/or antibacterial or antimicrobial substances. The wound dressing structure described herein may be applied to any type of wound dressing, including wound dressings both with and without absorbent components. For example, the layered structure described herein may be used in drapes, island dressings and/or dressings for use in negative pressure wound therapy, as well as any other types of wound dressings known in the art.

An island dressing is a wound dressing which comprises an absorbent pad or absorbent body surrounded by an adhesive portion. In use, wound exudate is absorbed by the absorbent pad to maintain a healthy wound environment and promote healing. Such a dressing typically comprises a backing layer, an absorbent pad or absorbent body and a wound contacting layer, such as a layer of perforated silicone gel. The backing layer and wound contacting layer extend beyond the edge of the absorbent pad on all sides, in order that the absorbent pad may cover the wound while the surrounding adhesive surface contacts and adheres to the healthy skin surrounding the wound. In accordance with the invention, a layer of moisture-permeable pressure-sensitive adhesive may be disposed either between the backing layer and the absorbent pad, covering the entire surface of the backing layer, or between the absorbent pad and the layer of perforated silicone gel. In either case, it is envisaged that the layer of pressure-sensitive adhesive extends across the whole surface of the wound dressing to which it is applied.

Any suitable absorbent material may be used as an absorbent pad in a wound dressing according to the invention. The absorbent pad may comprise a foam, a gelling material, a superabsorbent material (eg a superabsorbent polymer), or a combination of these components. The absorbent pad may comprise an absorbent laminate, formed of a layer of absorbent or superabsorbent material laminated between layers of tissue paper. A "superabsorbent material" in the context of the present invention means a material that is capable of absorbing many times its own mass of water (eg up to 200, 300, 400, 500 or more times its own mass of water).

The absorbent body may comprise a layered structure, and the wound dressing may comprise a plurality of absorbent bodies, eg 2, or 3, or 4 absorbent bodies stacked one on top of the other. A layered absorbent body may comprise a layer of absorbent material, eg an absorbent pad as described above, interleaved between one or more layers of carrier material. The one or more layers of carrier material may comprise wicking layer(s) to aid in drawing wound exudate away from the wound, and/or welding layers, to aid in adhering the layers of the absorbent body together. For example, a layer of superabsorbent material may be sandwiched between a layer of wicking material on its wound-facing side, and a layer of welding material on its non wound-facing side. A composite absorbent body may be formed by stacking together two or more absorbent bodies, each comprising a layer of wicking material, a layer of absorbent material, and a layer of welding material as previously described, the two or more absorbent bodies being bonded together via the layer(s) of welding material. Such a composite absorbent body may further comprise an additional carrier layer, eg a wicking layer, on its non wound contacting face, wherein the additional carrier layer is fused to the pressure sensitive adhesive carried on the backing layer.

An island wound dressing may be provided with an aperture or port in the backing layer located adjacent to the absorbent pad, to which a suction tube may be attached, so that the dressing may be used in negative pressure wound therapy (NPWT). The wound dressing may be supplied with the aperture covered by a releasable liner, which can be removed immediately prior to attachment of the suction tube. Alternatively, the releasable liner may be left in place and the dressing used as a conventional island dressing.

In a second aspect of the invention there is thus provided an island wound dressing comprising a backing layer, an absorbent pad and a wound contacting layer, the absorbent pad being disposed between the backing layer and the wound contacting layer, wherein the backing layer comprises an aperture which brings the absorbent pad into fluid communication with the exterior of the wound dressing.

The aperture may be located directly above or on top of the absorbent pad. The dressing may be supplied with the aperture occluded by a releasable liner, which may be made of siliconized paper or another suitable material. The aperture may be any shape suitable for connection to a suction tube, but is preferably circular. The aperture is of a size to enable it to be connected to a suction tube, and typically has a diameter of from 5 mm to 20 mm, or from 8 mm to 15 mm, or 10 mm to 14 mm. The island wound dressing according to this aspect of the invention may have a moisture-permeable layer of pressure-sensitive adhesive disposed between the backing layer and the absorbent pad, or between the absorbent pad and the wound contacting layer, as described in relation to earlier aspects of the invention. The wound contacting layer may be a layer of silicone gel, more preferably a layer of perforated silicone gel.

This aspect of the invention may comprise any of the features described in relation to the first aspect of the invention.

In this manner, a single wound dressing may be supplied which can be used both as a conventional island wound dressing, and as a wound dressing for use in NPWT.

The layer of pressure-sensitive adhesive discussed in relation to any of the previous aspects of the invention may be made moisture-permeable through application of the pressure-sensitive adhesive by fiberization.

Fiberization is a method of adhesive application known for use outside the medical field for the application of adhesives, and especially hot melt adhesives to laminate layers of material together. This method is known to allow a 20-50% reduction in the amount of adhesive without loss of bond strength or durability. However, it has now been found that fiberization may be used to create a moisture-permeable layer of adhesive on the surface of a substrate, for use in a wound dressing.

During the fiberization process, heated air is used to elongate monofilament strands of a hot-melt adhesive produced from a nozzle, creating a wall of fine adhesive fibres streaming onto the substrate and laying them down in a pattern of fibres in a continuous process. The resulting mat of fibres typically forms an open, net-like pattern. The pattern of fibres, weight of the coating, fibre size, density and pattern width can be controlled through control of the heated air flow and nozzle. Different patterns of adhesive may be achieved, and they may be random or ordered.

Machines for fiberization are commercially available, such as the ITW Dynatec UFD Spray Applicator. This is an air-operated, single or multi-module hot melt adhesive applicator assembly. The applicator is heated by a heating element, and a choice of adhesive inlets and an angled filter allows for either horizontal or vertical spray of the adhesive fibres. An adhesive valve on the applicator is opened and closed by air pressure, while the rate of adhesive flow from the applicator is determined by the adhesive pressure and the nozzle type. An air heater supplies heated air to fiberize the adhesive streams, which are then applied to a substrate.

This method of coating the adhesive results in an evenly coated, discontinuous and/or porous layer of adhesive which permits moisture transmission. On a microscopic level, an adhesive coating applied by a fiberization method has the appearance of a mat of fine fibres of adhesive with numerous, small, closely spaced apertures through which moisture vapour can egress.

Thus, according to a third aspect of the invention there is provided a method for the production of a wound dressing, said method comprising:

a) providing a backing layer;
b) applying a discontinuous layer of pressure-sensitive adhesive to the backing layer by fiberization, to form a moisture-permeable layer of pressure-sensitive adhesive; and
c) applying a perforated laminate comprising a layer of silicone gel and a substrate to the layer of pressure-sensitive adhesive.

Any of the features discussed in relation to the first aspect of the invention may be applied to this aspect. For example, an absorbent body may be included between the layers of pressure-sensitive adhesive and silicone gel to form an island dressing.

The backing layer provided in step a) may be any suitable substrate known in the art. The backing layer preferably has the form of a relatively thin film of a synthetic plastics material. A wide variety of plastics may be suitable for use as the structural layer, such as polyurethane, polyvinylchloride, polypropylene and regenerated cellulose.

The pressure-sensitive adhesive applied in step b) may be any one of numerous pressure-sensitive adhesives known in the art. Examples of pressure sensitive adhesives include rubber/resin adhesive, which is a mixture of a rubbery material and a hard resin, and acrylic (or acrylate) adhesives. The currently preferred class of pressure-sensitive adhesive for use in the present invention is acrylic adhesive.

Step c) may be accomplished in the manner described in WO 2007/113597. In general terms, this involves applying silicone gel precursors to a carrier, such as a sheet of melt-blown polyurethane (MBPU) or a polyurethane film, the underside of which carries a coating of acrylic adhesive and a temporary protective backing, eg of plastics film or paper. Once the silicone gel precursors have cured, to produce a hydrophobic silicone gel, a temporary cover, again of plastics film or paper material, is applied to the gel. Perforations are then formed in the pre-laminate. The temporary protective backing is removed from the underside of the carrier to expose the acrylic adhesive and the pre-laminate is applied to the product of step b). Finally, the temporary protective cover is removed from the silicone gel and replaced with an appropriately formed release liner, and individual dressings are punched out and sterile-packaged.

The invention will now be described in greater detail, by way of example only, with reference to the accompanying drawings, in which.

Figure 1:
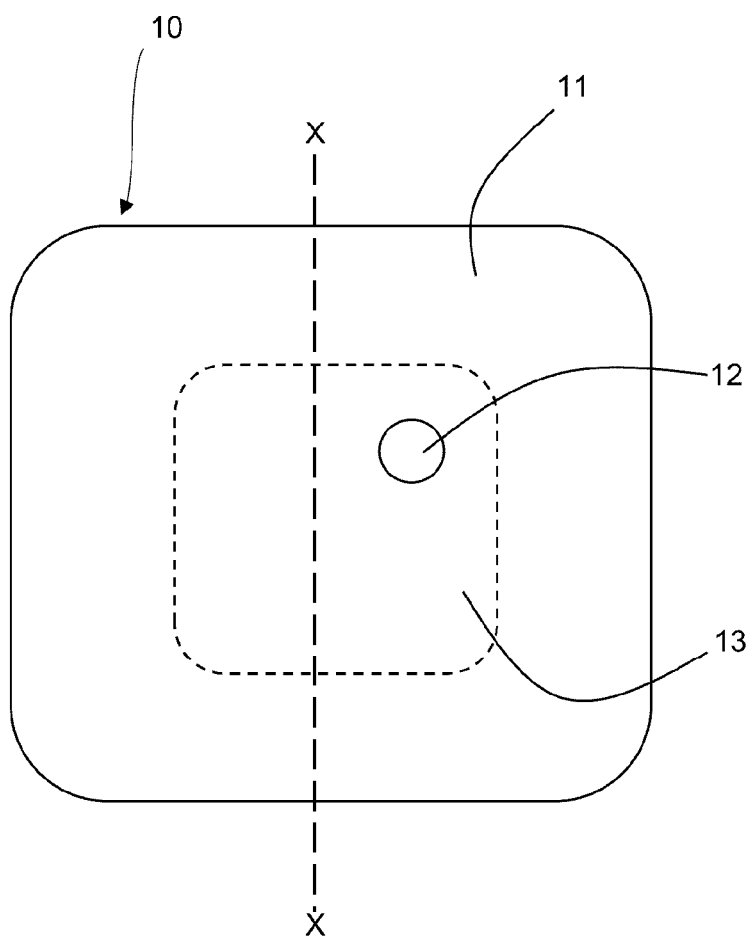
FIG. 1 is a schematic plan view of the top face of a wound dressing according to the invention.

FIG. 1 depicts a wound dressing 10 comprising a backing layer 11 formed of polyurethane film which overlays a sheet of an absorbent polyurethane foam pad 13 depicted by dashed lines. A circular hole in the backing layer above the superabsorbent material forms a port 12, which enables the wound dressing to be connected to a suction tube for use in NPWT. The dressing 10 is supplied with the port 12 covered by a releasable cover (not shown). The releasable cover may be left in place and the dressing used as a simple island dressing, or the releasable cover may be removed, exposing the port 12 and enabling the dressing to be used in NPWT.

Figure 2:
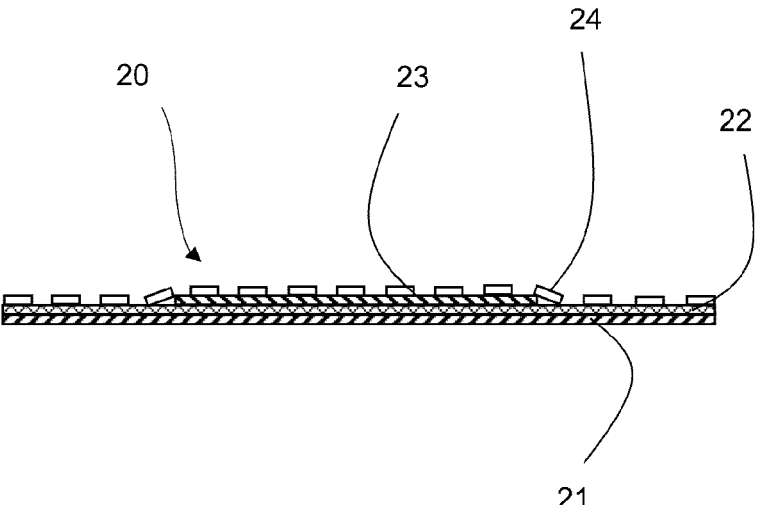
FIG. 2 is a cross-sectional view of the wound dressing of FIG. 1, taken along line X-X.

The layered structure of the wound dressing 10 is shown in FIG. 2, which shows a cross-section of the wound dressing of FIG. 1 taken along the line X-X. The polyurethane film backing layer 21 forms the top surface of the wound dressing which, in use, faces away from the wound. A moisture permeable layer of acrylic pressure-sensitive adhesive 22 is applied across the whole surface of the backing layer 21 by fiberization. This produces a discontinuous layer of adhesive having randomly arranged and irregularly shaped apertures across its surface, which permit the passage of moisture vapour through the pressure-sensitive adhesive. A pad of absorbent polyurethane foam material 23 is situated in the centre of the dressing 20 and is retained in place by the layer of pressure-sensitive adhesive 22. The adhesive layer 22 extends beyond the edge of the absorbent pad 23 on all sides, such that the superabsorbent pad 23 forms an island in the centre of the dressing 20. A perforated laminate 24 comprising a layer of perforated silicone gel overlays the absorbent pad 23 and pressure-sensitive adhesive layer 22, and forms the skin contact layer of the dressing 30. The perforated laminate 24 comprises a layer of silicone gel applied to a melt-blown polyurethane substrate.

Regions of the layer of pressure-sensitive adhesive 23 are thus exposed through the perforations in the laminate 24. When the dressing 20 is applied to a wound, these exposed regions of pressure-sensitive adhesive 23 contact the skin surrounding the wound, increasing adhesion of the wound dressing to the healthy skin. The discontinuous nature of the pressure-sensitive adhesive 23 permits the passage of moisture vapour through the dressing, which reduces the rate at which moisture builds up under the dressing.

The wound dressing may be supplied with a protective releasable liner (not shown) adhered to the silicone gel. The releasable liner is removed to expose the adhesive wound contacting face of the dressing immediately prior to application of the dressing to the wound site.

Figure 3:
FIG. 3 is a photograph of the wound contacting side of a wound dressing according to the invention.

The wound contacting layer can be seen in FIG. 3. The wound dressing 30 shown in FIG. 3 has the same layered structure as the wound dressings of FIGS. 1 and 2. It can be seen that the layer of perforated silicone gel 31 extends across the whole wound contacting surface of the wound dressing, while the pressure sensitive adhesive is exposed through the perforations in the silicone gel 32 in the area surrounding the sheet of superabsorbent material 33.

Figure 4A:
FIGS. 4a and 4b are photographs of a backing layer coated with a layer of pressure-sensitive adhesive.
Figure 4B:
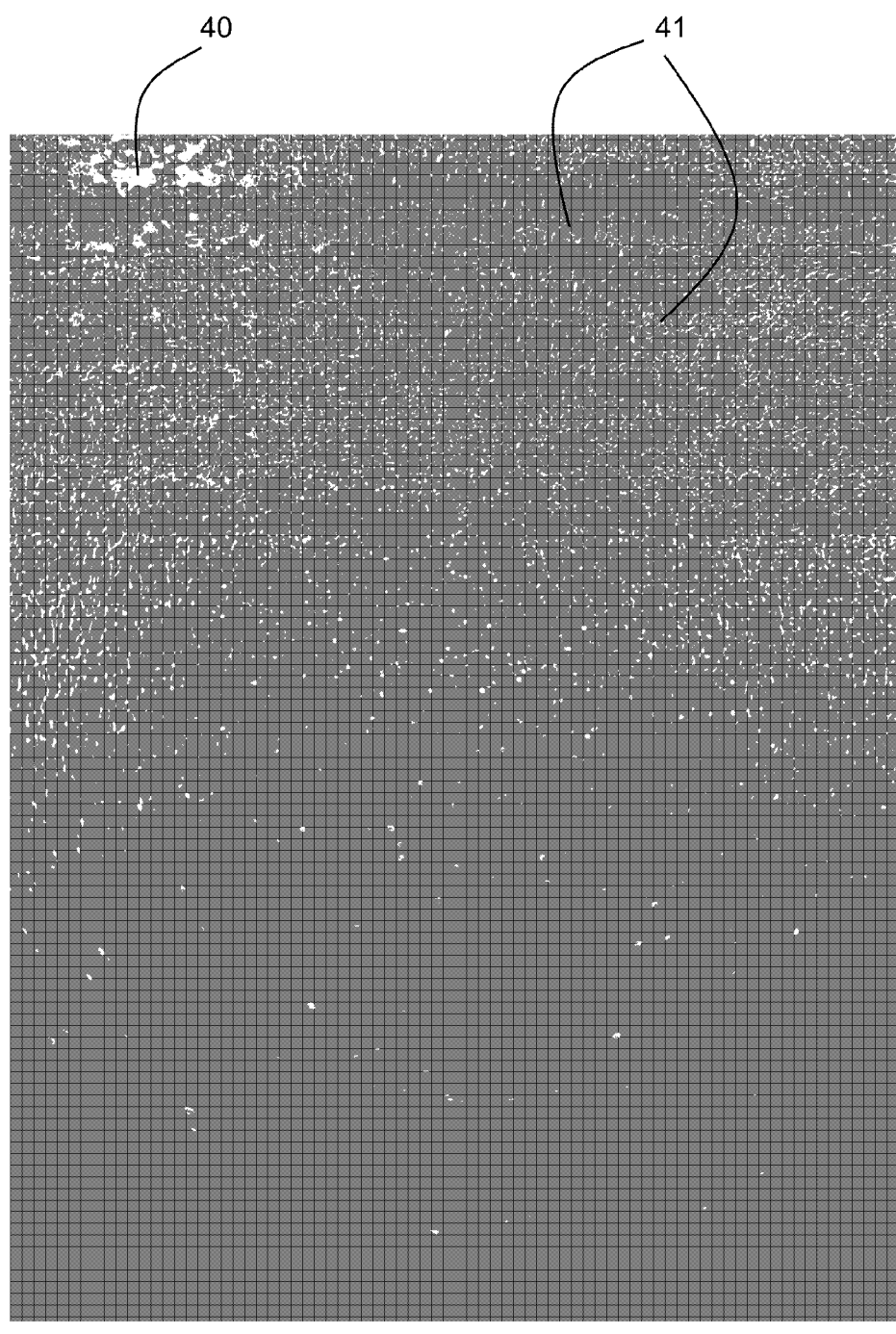

A layer of acrylic pressure-sensitive adhesive 40 applied by fiberization to a polyurethane film with a paper carrier is shown in FIGS. 4a and 4b. The use of fiberization results in a discontinuous layer of pressure-sensitive adhesive with numerous irregularly shaped, closely spaced apertures or gaps in the adhesive 41 through which moisture vapour can egress. It has the form of an open, net-like structure.

Figure 5:
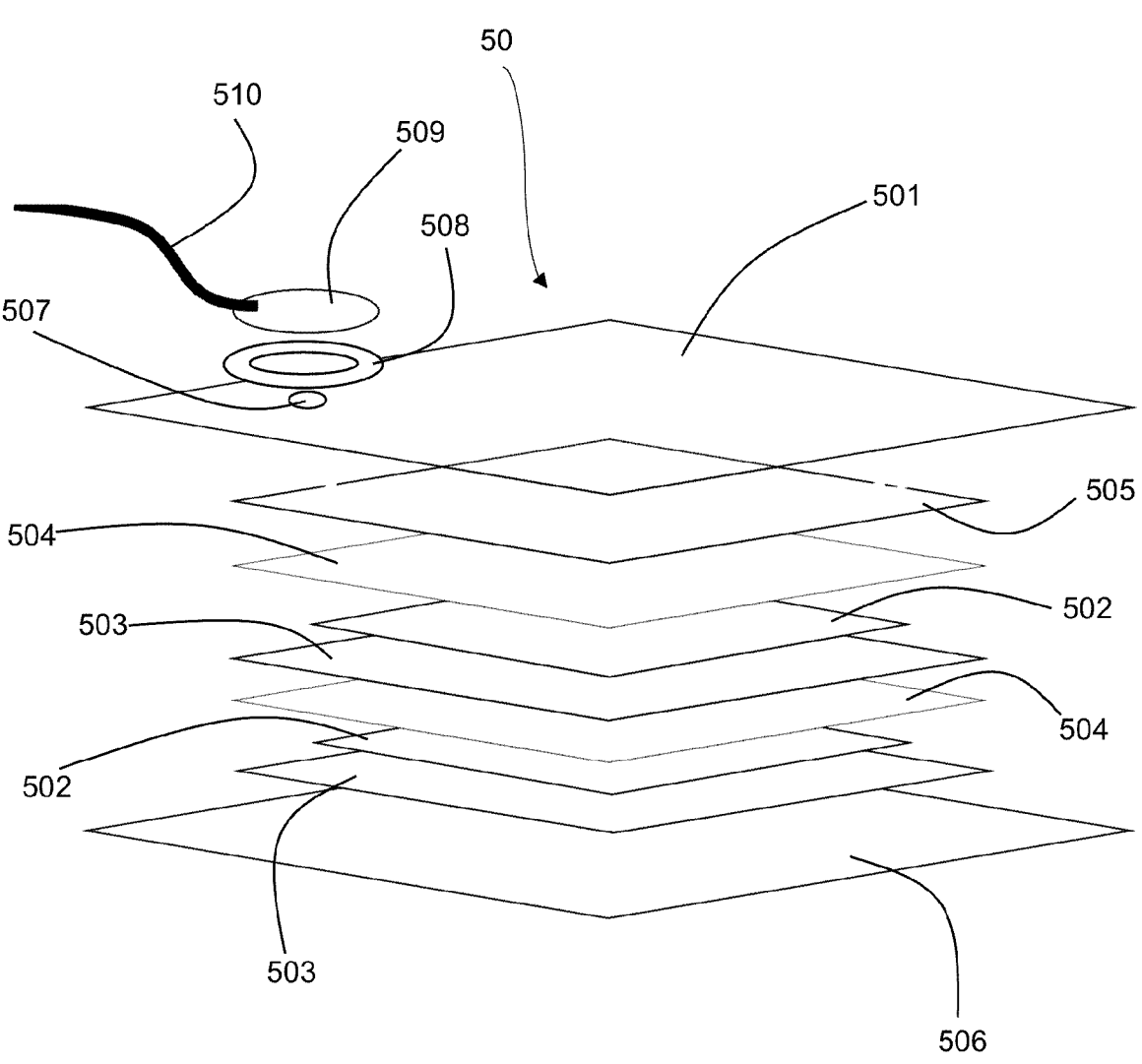
FIG. 5 is an explodied view of an island dressing according to the invention.

An island dressing 50 according to the invention may be seen in FIG. 5. The island dressing 50 comprises a backing layer of polyurethane film 501 coated with a layer of moisture-permeable pressure sensitive adhesive on its wound facing surface. The absorbent portion of the island dressing comprises a composite absorbent body, the composite absorbent body comprising two layers of a superabsorbent polymer 502, each layer of superabsorbent polymer 502 sandwiched between a layer of wicking material 503 on its underside and a layer of welding material 504 on its topside. This layered structure comprises a further layer of wicking material 505 on its non wound facing surface, and is fused to the backing layer 501.

The wound contacting surface of the wound dressing 50 carries a perforated laminate 506 comprising a layer of perforated silicone gel. The surface area of the composite absorbent body is smaller than the surface area of the backing layer 501 and perforated laminate 506, such that the backing layer 501 and perforated laminate 506 extend beyond the edges of the composite absorbent body on all sides. This ensures good adhesion of the wound dressing to the skin.

The backing layer 501 further comprises a port for connection to a vacuum for negative pressure wound therapy. The port comprises a circular aperture 507 in the backing layer 501, positioned above the composite absorbent body. The circular aperture 507 has a diameter of approximately 5 mm. The port further comprises an adhesive ring 508 positioned about the aperture 507. In use, a moulded connection pad 509, connected to a vacuum tube 510, is bonded to the adhesive ring 508. The port is positioned such that, in use, the moulded connection pad 509 sits entirely within the area of the composite absorbent body, to protect the patient's skin.

The dressing may be manufactured by the following general method.

First, a sheet of breathable polyurethane film (which constitutes the backing layer 11 of wound dressing 10) is coated with a layer of pressure sensitive adhesive using a fiberization process. An ITW Dynatec UFD Spray Applicator is used to apply a randomised, fibrous pattern of monofilament strands of an acrylic pressure-sensitive adhesive to one surface of the polyurethane film. An ordered pattern may alternatively be produced.

Second, a perforated laminate comprising a melt-blown polyurethane (MBPU) carrying silicone gel on one side and acrylic adhesive on the other is produced in the manner described in WO2007/113597. In general terms, this involves applying silicone gel precursors to a sheet of MBPU, the underside of which carries a coating of acrylic adhesive and a temporary protective backing, eg of plastics film or paper. Once the silicone gel precursors have cured, to produce a hydrophobic silicone gel, a temporary cover, again of plastics film or paper material, is applied to the gel. The perforations are then formed in the laminate by a suitable method. A preferred silicone gel for use in the wound dressing is Dow Corning™ 7-9700 Soft Skin Adhesive.

In a separate operation, the absorbent body is produced, and individual squares or other appropriate shapes are cut out. A preferred superabsorbent material for use in the absorbent body is polyurethane foam, although superabsorbent materials such as Gellok® 20040 S/S White may also be used.

The squares of the absorbent body are then positioned on the adhesive coated sheet of breathable polyurethane film. The temporary protective backing is removed from the underside of the MBPU to expose the acrylic adhesive and the laminate is applied to the polyurethane film. Finally, the temporary protective cover is removed from the silicone gel and replaced with appropriately formed release liners, and individual dressings 10, 20, 30 are punched out and sterile-packaged.

EXAMPLE

Comparison of the Moisture Vapour Transmission Rate of Polyurethane Films Carrying Different Coatings of Acrylic Adhesive The moisture vapour transmission rate (MVTR) of standard polyurethane (PU) films carrying a continuous flood coating of acrylic adhesive versus an irregular porous coating of acrylic adhesive produced by a fiberization method was compared.

The PU film carrying the irregular porous coating of acrylic adhesive was prepared by applying acrylic adhesive to the film using an ITW Dynatec UFD Spray Applicator.

The MVTR of the coated PU films were tested in accordance with the standard test methods for primary wound dressings set out in BS EN 13726-2:2002. In particular, deionised water was introduced into containers, the openings of the containers were sealed with samples of the coated PU film and the containers were weighted. The containers were then inverted such that the water remained in contact with the coated film and places in an incubator at a temperature of 37° C. A sufficient gap was maintained between the surface of the film samples and the incubator in order to ensure sufficient air flow across the surface of the film samples.

The containers were incubated for 4 hours under these conditions, following which they were removed from the incubator and weighed, with the reduction in weight indicating the amount of water that had been able to pass through the film during incubation. The experiment was repeated five times for PU film carrying each of a continuous flood coating of acrylic adhesive and an irregular porous coating of acrylic adhesive.

The mean reduction in weight was 309.08 g for the film carrying the continuous coating of acrylic adhesive and 814.82 g for the film carrying the irregular porous coating of acrylic adhesive. The ITW Dynatec UFD Spray Applicator is therefore able to apply an irregular porous coating of acrylic adhesive to a PU film that has a significantly higher MVTR than the same film carrying a continuous coating of adhesive while still providing effective adhesion.

The invention claimed is:

1. A wound dressing comprising a backing layer, a layer of pressure-sensitive adhesive and a perforated layer of silicone gel, wherein the layer of pressure-sensitive adhesive is disposed between the backing layer and the perforated layer of silicone gel, wherein the layer of pressure-sensitive adhesive is moisture-permeable, and wherein:

the layer of pressure-sensitive adhesive comprises apertures that are irregularly shaped and/or sized; and the layer of pressure-sensitive adhesive is formed from intermingling fibres of adhesive that form an irregular mat or mesh on the backing layer.

2. The wound dressing of claim 1, wherein the pressure-sensitive adhesive is rubber/resin adhesive, acrylic adhesive or acrylate adhesive.

3. The wound dressing of claim 1, wherein the layer of pressure-sensitive adhesive is applied to, and extends across a whole surface of, the backing layer.

4. The wound dressing of claim 1, wherein the layer of pressure-sensitive adhesive is a discontinuous layer of pressure-sensitive adhesive.

5. The wound dressing of claim 1, wherein the layer of pressure-sensitive adhesive comprises apertures having a mean average area of from 0.1 mm$^2$ to 5 mm$^2$, or from 0.1 mm$^2$ to 4 mm$^2$, or from 0.1 mm$^2$ to 3 mm$^2$.

6. The wound dressing of claim 5, wherein the apertures in the layer of pressure-sensitive adhesive account for at least 1%, at least 3%, at least 5%, at least 10%, at least 20%, or at least 30%, of the area covered by the pressure-sensitive adhesive and up to 80%, or up to 70%, or up to 60%, or up to 50%, or up to 40% of the area covered by the pressure-sensitive adhesive.

7. The wound dressing of claim 1, wherein the backing layer is a film of polyurethane, polyvinylchloride, polypropylene and regenerated cellulose.

8. The wound dressing of claim 1, wherein the perforated layer of silicone gel overlays the layer of pressure-sensitive adhesive and extends across a whole wound contacting surface of the wound dressing, forming a wound contacting layer.

9. The wound dressing of claim 1, wherein a coating weight of the silicone gel layer is less than 600 g/m$^2$, less than 400 g/m$^2$, less than 300 g/m$^2$ or about 200 g/m$^2$.

10. The wound dressing of claim 1, wherein the perforations in the layer of silicone gel have a diameter of between 1 mm and 15 mm, between 3 mm and 10 mm, between 5 mm and 8 mm, or about 6 mm.

11. The wound dressing of claim 1, wherein the silicone gel layer is carried on a substrate layer.

12. The wound dressing of claim 11, wherein the substrate layer is melt-blown polyurethane.

13. The wound dressing of claim 1, wherein the apertures of the layer of pressure-sensitive adhesive are irregularly shaped.

14. A method for production of a wound dressing, said method comprising:

a) providing a backing layer;

b) applying a discontinuous layer of pressure-sensitive adhesive to the backing layer by fiberization, to form a moisture-permeable layer of pressure-sensitive adhesive, which layer comprises apertures that are irregularly shaped and/or sized and is in the form of intermingling fibres of adhesive that form an irregular mat or mesh on the backing layer; and c) applying a perforated layer of silicone gel to the layer of pressure-sensitive adhesive.

15. The method of claim 14, wherein fiberization comprises extruding the adhesive into a stream of heated air and depositing the adhesive onto the substrate.

16. The method of claim 14, wherein the layer of pressure-sensitive adhesive comprises apertures having a mean average area of from 0.1 mm$^2$ to 5 mm$^2$, or from 0.1 mm$^2$ to 4 mm$^2$, or from 0.1 mm$^2$ to 3 mm$^2$.

17. The method of claim 14, wherein the apertures in the layer of pressure-sensitive adhesive account for at least 1%, at least 3%, at least 5%, at least 10%, at least 20%, or at least 30%, of the area covered by the pressure-sensitive adhesive and up to 80%, or up to 70%, or up to 60%, or up to 50%, or up to 40% of the area covered by the pressure-sensitive adhesive.

18. The method of claim 14, wherein the backing layer is a film of polyurethane, polyvinylchloride, polypropylene and regenerated cellulose.

19. The method of claim 14, wherein a coating weight of the silicone gel layer is less than 600 g/m$^2$, less than 400 g/m$^2$, less than 300 g/m$^2$ or about 200 g/m$^2$.

20. The method of claim 14, wherein the perforations in the layer of silicone gel have a diameter of between 1 mm and 15 mm, between 3 mm and 10 mm, between 5 mm and 8 mm, or about 6 mm.

21. The method of claim 14, wherein the perforated silicone gel layer is carried on a substrate layer and is adhered to the backing layer via the substrate.

22. The method of claim 21, wherein the substrate layer is melt-blown polyurethane.

23. The method of claim 14, wherein the apertures of the layer of pressure-sensitive adhesive are irregularly shaped.

* * * * *